(12) United States Patent
Miller et al.

(10) Patent No.: US 6,326,162 B1
(45) Date of Patent: Dec. 4, 2001

(54) ASSAYS AND PEPTIDE SUBSTRATE FOR DETERMINING AGGRECAN DEGRADING METALLO PROTEASE ACTIVITY

(75) Inventors: Jeffrey A. Miller, Lincoln University; Elizabeth C. Arner, West Grove, both of PA (US); Robert A. Copeland, Hockessin, DE (US); Gary L. Davis, Claymont, DE (US); Ruiqin Liu, Hockessin, DE (US); Michael Pratta, Glassboro, NJ (US); Micky D. Tortorella, Newark, DE (US)

(73) Assignee: Bristol-Myers Squibb Pharma Company, Princeton, NJ (US)

( * ) Notice: Subject to any disclaimer, the term of this patent is extended or adjusted under 35 U.S.C. 154(b) by 0 days.

(21) Appl. No.: 09/122,127

(22) Filed: Jul. 24, 1998

Related U.S. Application Data
(60) Provisional application No. 60/053,850, filed on Jul. 25, 1997, provisional application No. 60/055,836, filed on Aug. 15, 1997, and provisional application No. 60/062,169, filed on Oct. 16, 1997.

(51) Int. Cl.$^7$ ..................................... C12Q 1/37
(52) U.S. Cl. ................. 435/23; 435/4; 435/183; 435/219; 435/226; 530/300
(58) Field of Search ................. 435/4, 23, 183, 435/219, 226; 530/300

(56) References Cited

FOREIGN PATENT DOCUMENTS

| 0785274 | 7/1997 | (EP) . |
| 0785274A1 * | 7/1997 | (EP) . |
| 9322429 | 11/1993 | (WO) . |
| 9601847 | 1/1996 | (WO) . |
| 9725437 | 7/1997 | (WO) . |

OTHER PUBLICATIONS

Mankin et al., 1970, J. Bone Joint Surg. 52A, 424–434.
Paulson et al. 1987, Biochem. J., 245, 763–772.
Hardingham et al. 1972, Biochem. Biophys. Acta, 279, 401–405.
Heinegard et al. 1974, J. Biol. Chem., 249, 4250–4256.
Hardingham, T. E., 1979, Biochem. J., 177, 237–247.
Flannery et al. 1992, J. Biol. Chem., 267, 1008–1014.
Sandy et al. 1992, J. Clin. Invest., 89, 1512–1516.
Lohmander et al. 1993, Arthritis Rheum., 36, 1214–1222.
Sandy et al. 1991, J. Biol. Chem. 266, 8198.
Sandy et. al. 1991, J. Biol. Chem. 266, 8683–8685.
Loulakis et al. 1992, Biochem. J., 284, 589–593.
Ilic et al. 1992, Arch. Biochem. Biophys., 294, 115–122.
Lark et al. 1995, J. Biol. Chem., 270, 2550–2556.
Fosang et al. 1992, J. Biol. Chem., 267, 19470–19474.
Fosang et al. 1993, Biochem J. 295, 273–276.
Fosang et al. 1996, FEBS Lett. 380, 17–20.
Flannery et al. 1993, Orthop. Trans. 17, 677.
Fosang et al. 1994, Biochem. J., 304, 347–351.
Sandy et al. 1995, Acta Orthop Scand, (Suppl. 266) 66, 26–32.
Hughes et al. 1995, J. Biochem. 306, 799–804.
EMBL/Genebank Databases, Access No. P13608, Sequence reference PGCA_Bovin, Jan. 1, 1990.

* cited by examiner

*Primary Examiner*—Ponnathapu Achutamurthy
*Assistant Examiner*—Christian L. Fronda
(74) *Attorney, Agent, or Firm*—Karen Konrad; Kenneth B. Rubin; Kalim S. Fuzail (57) ABSTRACT

This invention is directed to assays to determine the presence or absence of proteins that exhibit aggrecanase or ADMP activity. This invention also relates to peptides that acts as a substrates for ADMPs, their use in various assays to determine the presence or absence of ADMP activity, and their use as inhibitors of ADMP activity.

2 Claims, 3 Drawing Sheets

ASSAYS AND PEPTIDE SUBSTRATE FOR DETERMINING AGGRECAN DEGRADING METALLO PROTEASE ACTIVITY

CROSS REFERENCE TO EARLIER FILED APPLICATION

This application claims the benefit of U.S. Provisional Application No. 60/053,850 filed on Jul. 25, 1997 and U.S. Provisional Application No. 60/055,836 filed on Aug. 15, 1997 and U.S. Provisional Application No. 60/062,169 (unknown at filing), filed on October 16, 1997.

FIELD OF THE INVENTION

This invention is directed to various assays for determining aggrecanase or aggrecan degrading metallo protease (ADMP) activity. This invention also relates to a peptide that acts as a substrate for ADMPs, its use in various assays to determine the presence or absence of (ADMP) activity, and its use as an inhibitor of ADMP activity.

BACKGROUND OF THE INVENTION

Aggrecan is the major proteoglycan of cartilage and provides this tissue with its mechanical properties of compressibility and elasticity. In arthritic conditions one of the earliest changes observed in cartilage morphology is the depletion of aggrecan [Mankin et al. (1970) J. Bone Joint Surg. 52A, 424–434], which appears to be due to an increased rate of degradation.

The aggrecan molecule is composed of two N-terminal globular domains, G1 and G2, which are separated by an approximately 150 residue interglobular domain (IGD), followed by a long central glycosaminoglycan (GAG) attachment region and a C-terminal globular domain, G3 [Hardingham et al. (1992) in Articular Cartilage and Osteoarthritis: Aggrecan, The Chondroitin Sulfate/Keratan Sulfate Proteoglycan from Cartilage (Kuettner et al.) pp. 5–20, Raven Press, New York and Paulson et al. (1987) Biochem. J. 245, 763–772]. These aggrecan molecules interact through the G1 domain with hyaluronic acid and a link protein to form large molecular weight aggregates which are trapped within the cartilage matrix [Hardingham et al. (1972) Biochim. Biophys. Acta 279, 401–405, Heinegard et al. (1974) J. Biol. Chem. 249, 4250–4256, and Hardingham, T. E. (1979) Biochem. J. 177, 237–247]. Loss of aggrecan from cartilage in arthritic conditions involves proteolytic cleavage of the aggrecan core protein within the IGD, producing a N-terminal G-1 fragment that remains bound to hyaluronic acid and the link protein within the matrix, releasing a large C-terminal GAG-containing aggrecan fragment that diffuses out of the cartilage matrix. Loss of the C-terminal fragment results in cartilage deficient in its mechanical properties. This deficiency arises because the GAGs which are present on the C-terminal portion of the aggrecan core protein are the components of aggrecan that impart the mechanical properties to the molecule through their high negative charge and water binding capacity.

Two major sites of proteolytic cleavage have been identified within the IGD, one between amino acid residues $Asn^{341}$-$Phe^{342}$ and the other between amino acid residues $Glu^{373}$-$Ala^{374}$ (human sequence enumeration). Although G1 fragments formed by cleavage at the $Asn^{341}$-$Phe^{342}$ site and at the $Glu^{373}$-$Ala^{374}$ site have been identified within articular cartilage [Flannery et al. (1992) J. Biol. Chem. 267, 1008–1014], the only N-terminus identified on GAG-containing aggrecan C-terminal aggrecan fragments in synovial fluids of patients with osteoarthritis [Sandy et al. (1992) J. Clin. Invest. 69, 1512–1516], inflammatory joint disease [Lohmander et al. (1993) Arthritis Rheum. 36, 1214–1222] and in the media from cartilage explant and chondrocyte cultures stimulated with interleukin-1 or retinoic acid [Sandy et al. (1991) J. Biol. Chem. 266, 8198., Sandy et al. (1991) J. Biol. Chem. 266, 8683–8685., Leulakis et al. (1992) Biochem. J. 264, 589–593., Ilic et al. (1992) Arch. Biochem. Biophys. 294, 115–122., Lark et al. (1995) J. Biol. Chem. 270, 2550–2556. ] is ARGSVIL, indicating that they were formed by cleavage between amino acid residues $Glu^{373}$-$Ala^{374}$. These observations suggest that cleavage at this site may be responsible for cartilage degradation.

Although many matrix metalloproteases (MMP-1, -2, -3, -7, -8, -9 and 13) have been shown to cleave in vitro at the $Asn^{341}$-$Phe^{342}$ site, digestion of aggrecan with a number of these purified proteases has not resulted in cleavage at the $Glu^{373}$-$Ala^{374}$ site [Fosang et al. (1992) J. Biol. Chem. 267, 19470–19474., Flannery et al. (1992) J. Biol. Chem. 267, 1008–1014., Fosang et al. (1993) Biochem. J. 295, 273–276., Fosang et al. (1996) FEBS Lett. 380, 17–20., Flannery et al. (1993) Orthop. Trans. 17, 677., and Fosang et al. (1994) Biochem. J. 305, 347–351]. Therefore, cleavage at this site has been attributed to a novel, proteolytic activity, "aggrecanase".

In addition to the $Glu^{373}$-$Ala^{374}$ bond within the interglobular domain of aggrecan, four potential aggrecanase-sensitive sites have been identified within the C-terminus of the aggrecan core protein [Loulakis et al. (1992) Biochem. J. 264, 589–593. and Sandy et al. (1995) Acta Orhtop Scand (Suppl 266) 66, 26–32]. Although cleavage at these sites which are not within the interglobular domain would not be expected to release the major portion of the aggrecan molecule from the matrix, they may be involved in earlier processing of aggrecan within the matrix.

It follows from the foregoing considerations that a sensitive and specific assay that can detect such aggrecanase activity of aggrecan degrading metallo proteases (ADMPs) would be beneficial in helping to identify inhibitors of members of the ADMP family, which could serve as potential therapeutic agents for treating aggrecanase-related disorders cited above.

SUMMARY OF THE INVENTION

A preferred embodiment of the invention provides assays that determine the presence of aggrecan degrading metallo protease (ADMP) activity.

A preferred embodiment of the invention provides an assay using purified native aggrecan or recombinant aggrecan as the substrate and monitoring product generation via a direct enzyme-linked immunosorbent assay (ELISA) using neoepitope antibodies to detect the new N-terminus or new C-terminus on aggrecan fragments formed by specific cleavage at an ADMP-sensitive site in the aggrecan core protein.

A preferred embodiment of the invention provides peptides that have been found to act as substrates for the family of aggrecan degrading metallo proteases (ADMPs). One peptide, based on the human aggrecan sequence around the Ala373-Glu374 ADMP-sensitive site has the sequence:

QTVTWPDMELPLPRNITEGE-
ARGSVILTVKPIFEVSPSPL (SEQ ID No:1)

A second peptide, based on the bovine aggrecan sequence around the Ala373-Glu374 ADMP-sensitive site has the sequence:

QTVTWPDVELPLPRNITEGE-
ARGSVILTAKPDFEVSPTAPE (SEQ ID NO:2) Both peptides are capable of being cleaved at this specific recognition site by members of the family of ADMP proteins. A third peptide, based on the human aggrecan sequence around the Ala11714-Gly11715 ADMP-sensitive site has the sequence:

ITFVDTSLVEVTPTTFKEEE-
GLGSVELSGLPSGELGVSGT (SEQ ID NO:3)

and is capable of being cleaved at this specific recognition site by the family of ADMP proteins.

A preferred embodiment of the invention provides assay formats and methods of utilizing these peptide substrates for the detection and quantification of ADMP activity.

A preferred embodiment of the invention provides a modified version of the peptide substrates and a method for their use as an inhibitor of ADMP activity.

BRIEF DESCRIPTION OF THE DRAWINGS

Preferred embodiments of the invention have been chosen for purposes of illustration and description, but are not intended in any way to restrict the scope of the invention. The preferred embodiments of certain aspects of the invention are shown in the accompanying drawings described below.

DETAILED DESCRIPTION OF THE INVENTION

A family of aggrecan degrading metallo protease (ADMP) proteins cleave the aggrecan core protein at the $Glu^{373}$-$Ala^{374}$ peptide bond and thus exhibit the enzymatic activity referred to as "aggrecanase" activity [Flannery et al. (1992) J. Biol. Chem. 267, 1008–1014]. The presence of ADMP enzymatic activity can be determined by monitoring the production of aggrecan fragments generated exclusively by cleavage at the $Glu^{373}$-$Ala^{374}$ peptide bond within the aggrecan core protein. These aggrecan fragments are detected by using neoepitope antibodies to the new N-terminus or new C-terminus on fragments produced by specific cleavage at this ADMP-sensitive site. The neoepitope antibodies used encompase but are not limited to, the BC-3 monoclonal antibody (Hughes, C. E., et al., Biochem. J. 306:799–804, 1995) as first described in U.S. Provisional Patent Application Serial No. 60/006,684 and subsequently described in U.S. patent application Ser. No. 08/743,439.

ADMP activity may also be detected by monitoring the production of fragments formed by cleavage at alternative ADMP-sensitive sites using neoepitope antibodies to the new C-terminus or to the new N-terminus generated by ADMP-specific cleavage at these sites. Alternative sites in the aggrecan core protein encompass, but are not limited to, the E1545-G1546, E1714-G1715, E1819-A1820, or E1919-L1920 bond (numbering based on the human aggrecan core protein sequence.

A preferred assay format involves using purified native aggrecan or recombinant aggrecan as the substrate with product detection via a direct enzyme-linked immunosorbent assay (ELISA), herein referred to as the "Problot assay", using neoepitope antibodies to the new C-terminus or new N-terminus on aggrecan fragments generated upon specific cleavage at ADMP-sensitive sites within the aggrecan core protein. Alternative sites in the aggrecan core protein encompass, but are not limited to, the E1545-G1546, E1714-G1715, E1819-A1820, or E1919-L1920 bond (numbering based on the human aggrecan core protein sequence). These human aggrecan ADMP-senstitive cleavage sites are conserved in aggrecan from various animal species although the absolute numbering based on the sequence of the aggrecan core protein may vary from species to species. Conserved amino acid sequences in various species around conserved ADMP-sensitive sites are shown below.

| Human | NITEGE$^{373}$ | $^{374}$ARGSVILT |
|---|---|---|
| Bovine | NITEGE | ARGSVILT |
| Rat | NITEGE | ARGNVILT |
| Mouse | NVTEGE | ALGSVILT |
| Pig | NITEGE | ARGTVILT |
| Sheep | NITEGE | ARGNVILT |
| Chicken | NVTEEE | ARGSI |
| Horse | NITEGE | ARGNVILT |
| Human | ASTASELE$^{1545}$ | $^{1546}$GRGTIGIS |
| Bovine | ATTAGELE | GRGTIDIS |
| Mouse | ATTSSELE | GRGTIGIS |
| Rat | ATTASELE | GRGTISVS |
| Human | PTTFKEEE$^{1714}$ | $^{1715}$GLGSVELS |
| Bovine | PTTFKEEE | GLGSVELS |
| Rat | PTTFREEE | GLGSVELS |
| Mouse | PTTFREEE | GLGSVELS |
| Human | TQAPTAQE$^{1819}$ | $^{1820}$AGEGPSGI |
| Bovine | TQAPTAQE | AGEGPSGI |
| Rat | TLAPTAQE | AGEGPSSI |
| Mouse | TQAPTAQE | AGEGPSGI |
| Chicken | TQTSVAQE | VGEGPSGM |
| Human | TEPTISQE$^{1919}$ | $^{1920}$LGQRPPVT |
| Bovine | TEPTVSQE | LGQRPPVT |
| Rat | TEPTVSQE | LGHGPSMT |
| Mouse | TEPTVSQE | LGHGPSMT |
| Chicken | TRPTVSQE | LGGETAVT |
| Dog | TEPTVSQE | LAQRPPVT |

Thus, aggrecan from various animal species, including but not limited to, bovine, dog, pig, rat, mouse, sheep, horse and chicken may also be used as a substrate for detecting ADMP activity.

The direct ELISA assay employs 96-well filtration plates containing polyvinyl-denedifluoride (PVDF) cationically charged membranes. These membranes are semi-selective in binding the highly negatively-charged aggrecan, which allows for binding of detectable levels of neoepitope antibody-reactive aggrecan fragments from solutions containing high levels of other proteins.

Utilizing neoepitope antibodies allows detection of fragments formed specifically by ADMP-mediated cleavage even in the presence of other proteolytic activities which may be present in crude preparations. Thus, the Problot assay can be used to monitor ADMP activity in culture medium containing other proteases, as well as to monitor the activity of the purified ADMP enzyme. Therefore, this assay has particular use in following ADMP activity during purification from tissue or media samples as well as for use in enzymatic assays to evaluate inhibitors of the ADMP enzyme. The Problot assay can also be used to detect ADMP-generated aggrecan fragments in culture media from tissue or cell cultures stimulated to induce ADMP-mediated degradation. This assay may also be useful for detecting ADMP-generated aggrecan fragments in cartilage, synovial fluid, serum, urine or other biological samples from patients with ADMP-associated diseases.

Peptide substrates are commonly employed in a variety of assays to determine the presence of enzymes that catalyze the hydrolysis of proteins. One skilled in the art would rely on the use of peptide substrates that are relatively short in length, generally consisting of approximately six to ten amino acids in length. These peptide substrates typically encompass amino acid sequences that bracket the known hydrolysis site of the natural protein substrates. These peptide substrates, including those for matrix metalloproteases, serine proteases, aspartyl proteases, and aminopeptidases, are readily available for use in a variety of enzymatic assays.

This invention provides a peptide that has been found to act as a substrate for the family of ADMPs. It is commonly known that short peptide sequences which contain the proper substrate cleavage site are quite acceptable substrates for many proteases (Copeland, R. A., Enzymes: A Practical Introduction to Structure, Mechanism and Data Analysis, VCH/Wiley, New York, 1996). However, no such peptide, even those containing as many as twenty amino acids, has been determined that will act as a suitable substrate for ADMPs. The peptides of the instant invention are unique in that it was unexpectedly found that these longer, forty amino acid sequence acted as very good substrates for ADMPs. One such peptide provided by the invention, of the sequence QTVTWPDMELPLPRNITEGE-
ARGSVILTVKPIFEVSPSPL (SEQ ID NO:1) comprises a 40 amino acid segment of the human aggrecan protein that contains the ITEGE373–374ARGS cleavage site present in the natural protein substrate, aggrecan, and is capable of being cleaved at this specific recognition site by the ADMPs. Since the human aggrecan ADMP-senstitive cleavage sites are conserved in aggrecan from various animal species, peptides based on the amino acid sequence around the ADMP-sensitive cleavage sites from other species can also serve as substrates for ADMPs. A peptide substrate, similar to SEQ ID NO:1, based on a 41 amino acid segment of the bovine aggrecan protein, of the sequence QTVTWPDVELPLPRNITEGE-
ARGSVILTAKPDFEVSPTAPE (SEQ ID NO:2)
containing the E373-A374 cleavage site is also capable of being cleaved at this specific recognition site by the ADMPs.

Cleavage products are easily detected by using neoepitope antibodies to the N-terminal or C-terminal fragments produced by specific cleavage at the E373-A374 bond, encompasing, but not limited to, the monoclonal antibody BC-3 (Hughes, C. E., et al., Biochem. J. 306:799–804, 1995). The BC-3 antibody recognizes the new N-terminus, ARGS, which is the amino terminal portion of one of the product peptides resulting from the ADMP activity of the enzyme.

One skilled in the art could readily design peptides of similar size encompasing the alternative ADMP-sensitive cleavage sites in the aggrecan core protein, encompasing, but not limited to, regions of the molecule containing the E1545-G1546, E1714-G1715, E1819-Al820, or E1919-L1920 bond (numbering based on the human aggrecan core protein sequence). One such peptide provided by the invention, of the sequence

ITFVDTSLVEVTPTTFKEEE-
GLGSVELSGLPSGELGVSGT (SEQ ID NO:3)

comprises a 40 amino acid segment of the human aggrecan protein that contains the KEEE1714–1715GLGS cleavage site present in the natural protein substrate, aggrecan, and is capable of being cleaved at this specific recognition site by the ADMPs.

When a preferred form of a peptide substrate, biotinylated at the carboxy terminus or amino terminus, is employed, several streptavidin coated supports may be used. These include, but are not limited to, microplates, metallic and non-metallic beads, and membranes.

Another preferred assay format involves the direct analysis, by high-performance liquid chromatography (HPLC), of the cleavage fragments from the substrate that are generated by ADMP activity.

Another preferred embodiment of the invention provides that a peptide substrate of this invention may be reversed in its role. With proper modification at the P1 position the substrate may be turned into an inhibitor of ADMP activity. Specifically it was found that esterification of the P1 glutamic acid residue ($GLU^{373}$) of the substrate peptide SEQ ID NO:1 or its replacement by glutamine abolish catalytic hydrolysis. Unexpectedly, the peptide containing the GLU to GLN substitution at amino acid position 373 (the P1-glutamine containing peptide) was shown to be a competitive inhibitor of the enzyme. Thus, a carboxylate residue at position P1 of the substrate appears to be critical for turnover by ADMPs, but exerts less influence over initial substrate binding to the enzyme. This feature can be readily exploited by one trained in the art to design specific peptide and non-peptide inhibitors of this enzyme.

DEFINITIONS

As used herein, the following terms and expressions have the indicated meanings.

The term "aggrecan degrading metallo protease" ("ADMP") activity as referred to herein, refers to the enzymatic activity of a family of polypeptides which specifically cleave the protein aggrecan within the interglobular domain at the $Glu^{373}$-$Ala^{374}$ peptide bond, but do not readily cleave at the Asn341-Phe342 bond which is preferentially cleaved by matrix metalloproteinases.

The term "amino acid" as used herein means an organic compound containing both a basic amino group and an acidic carboxyl group.

The term "amino acid residue" as used herein means that portion of an amino acid (as defined herein) that is present in a peptide.

The term "peptide" as used herein means a compound that consists of two or more amino acids (as defined herein) that are linked by means of a peptide bond. The term "peptide" also includes compounds containing both peptide and non-peptide components, such as pseudopeptide or peptide mimetic residues or other non-amino acid components. Such a compound containing both peptide and non-peptide components may also be referred to as a "peptide analog".

The term "peptide bond" means a covalent amide linkage formed by loss of a molecule of water between the carboxyl group of one amino acid and the amino group of a second amino acid.

The term "substrate" refers to a molecule that is bound by the active site and acted upon by the enzyme.

The term "solid-phase peptide synthesis" refers to the direct chemical synthesis of peptides utilizing an insoluble polymeric support as the anchor for the growing peptide, which is built up one amino acid at a time using a standard set of reactions in a repeating cycle (Merrifield, R. B., Science 232, 341–347 1986).

As used herein, the term "TMB" refers to 3,3', 5,5'-tetramethylbenzidine.

The term "neoepitope antibody" refers to an antibody which specifically recognizes a new N-terminal amino acid sequence or new C-terminal amino acid sequence generated by proteolytic cleavage but does not recognize these same sequences of amino acids when they are present within the intact protein.

As used herein, the cleavage site "E373–374A" refers to the ITEGE373–374ARGS bond of human aggrecan as well as to the homologous aggrecanase-sensitive cleavage site in aggrecan from various animal species, the cleavage site "E1545–1546G" refers to the SELE1545–1546GRGT bond of human aggrecan as well as to the homologous aggrecanase-sensitive cleavage site in aggrecan from various animal species, the cleavage site "E1714–1715G" refers to the KEEE1714–1715GLGS bond of human aggrecan as well as to the homologous aggrecanase-sensitive cleavage site in aggrecan from various animal species the cleavage site "E1819–1820A" refers to the TAQE1819–1820AGEG bond of human aggrecan as well as to the homologous aggrecanase-sensitive cleavage site in aggrecan from various animal species, the cleavage site "E1919–1920L" refers to the ISQE1919–1920LGQR bond of human aggrecan as well as to the homologous aggrecanase-sensitive cleavage site in aggrecan from various animal species.

The term "aggrecan" as used herein refers to the aggregating proteoglycan, aggrecan, of cartilage from human or various animal species, as the native aggrecan isolated from tissue, as recombinant full-length aggrecan or as a recombinant protein representing a portion of the aggrecan molecule.

As used herein the term "ADMP-susceptible cleavage site" refers to the E373–374A bond, the E1545–1546G bond, the E1545–1546G bond, the E1819–1820A bond, and the E1919-1920L bond of aggrecan from human and various animal species, and to a peptide bond of a protein containing an amino acid sequence which has a glutamine in the P1 position and shows at least 65% homology with the P1, P2, P3, P1', P2' and P3' amino acids of one or more of the ADMP-sensitive sites in the aggrecan molecule.

The term "sissel bond" refers to the peptide bond of a polypeptide that is to be cleaved by a protease. The term "P1" as used herein refers to the amino acid residue on the N-terminal side of the sissel bond. The term "P2" as used herein refers to the amino acid residue adjacent to P1 on the N-terminal side of the sissel bond. The term "P3" as used herein refers to the amino acid residue adjacent to P2 on the N-terminal side of the sissel bond. The term "P1'" as used herein refers to the amino acid residue on the C-terminal side of the sissel bond. The term "P2'" as used herein refers to the amino acid residue adjacent to P1' on the C-terminal side of the sissel bond. The term "P3'" as used herein refers to the amino acid residue adjacent to P2' on the C-terminal side of the sissel bond.

The term "BC-3 antibody" refers to a monoclonal antibody that reacts specifically with the newly-formed amino-terminal sequence ARGS on fragments produced by proteolytic cleavage at the Glu$^{373}$-Ala$^{374}$ aggrecan cleavage site, but does not recognize this same sequence of amino acids when they are present within the intact interglobular domain of the protein (Hughes, C. E., et al., Biochem. J. 306:799–804, 1995).

The term "SEQ ID NO:1" refers to the peptide sequence QTVTWPDMELPLPRNITEGE-ARGSVILTVKPIFEVSPSPL. The term "SEQ ID NO:2" refers to the peptide sequence QTVTWPDVELPLPRNITEGE-ARGSVILTAKPDFEVSPTAPE. The term "SEQ ID NO:3" refers to the peptide sequence ITFVDTSLVEVTPTTFKEEE-GLGSVELSGLPSGELGVSGT. The term "41-PS" and "SEQ ID NO:4" refer to the peptide sequence: QTVTWP-DMELPLPRNITEGEARGSVILTVKPIFEVSP SPL-(BIOTINYL)K. The term "SEQ ID NO:5" refers to the peptide sequence: ARGSVILTVKPIFEVSPSPL-(BIOTINYL)K. The term "SEQ ID NO:6" refers to the peptide sequence: K(BIOTINYL)-QTVTWPDMELPLPRNITEGE. The term "30-IP" and "SEQ ID NO:7" refer to the peptide sequence QTVTWPDMELPLPRNITEGQARGSVILTV-(BIOTINYL)K.

The invention can be further understood by the following examples. These examples provide an illustration of embodiments of the invention and should not be construed to limit the scope of the invention which is set forth in the appended claims. In the following examples all methods described are conventional unless otherwise specified.

Example 1

Microplate Assay Format for Detection of ADMP Activity

The substrate and product peptides were prepared in the following manner. A 41 amino acid form (41-PS) SEQ ID NO:4 of the peptide substrate SEQ ID NO:1 was prepared by solid phase peptide synthesis. The peptide was prepared commercially (Quality Controlled Biochemicals, Inc. Hopkinton, Mass.) as a biotin conjugate by adding an additional lysine residue at the carboxy terminus of the peptide SEQ ID NO:1. Biotin was then covalently attached through the lysine ε-amino side chain. 41-PS sequence:

QTVTWPDMELPLPRNITEGE-ARGSVILTVKPIFEVSPSPL-(BIOTINYL)K (SEQ ID NO:4) A 21 amino acid peptide representing the product of ADMP-mediated cleavage of the 41-PS containing the ARGS N-terminus was prepared in a similar manner and had the following sequence:

ARGSVILTVKPIFEVSPSPL-(BIOTINYL)K (SEQ ID NO:5)

The substrate and product peptide microplates were prepared in the following manner. A 0.1 mM stock of 41-PS was made by dissolving it in distilled water. From this a working solution of 7×10$^{-8}$ M 41-PS was prepared in 1×PBS, 0.05% Tween 20. Aliquots of 100 μL of this solution were added to the microplate wells of a streptavidin coated microtiter strip plate (DUPONT, NEN Products, Catalog # NEF-711). The solutions were allowed to sit at 25° C. overnight in order for the biotin moiety of the peptides to bind to the streptavidin which was coated on the microplate. The plate was washed three times with 200 μL of 1×PBS, 0.05% Tween 20, after which the plate was inverted, blotted dry, sealed and stored at 4° C.

The assay was performed in the following manner. Microplate strips (eight wells each) were rinsed once with 100 μL of 1×Assay Buffer (Assay Buffer consists of: 50 mM Tris, pH 7.5, 10 mM CaCl$_2$, and 100 mM NaCl) and blotted dry. Reactions were prepared in duplicate in a final volume of 100 μL, containing: 50 μL of 2×Assay Buffer (100 mM Tris, pH 7.5, 20 mM CaCl$_2$, and 200 mM NaCl), 25 μL of a hydroxymate inhibitor compound (final concentrations consisting of 5.0, 1.0, 0.75, 0.5, 0.25, 0.125, 0.05, 0.001, and 0.0 μM), and 25 μL of soluble ADMP (0.05 ηM). The microplate strips were incubated for 3 hours at 37° C. The microplate wells were then washed six times with 200 μL of 1×PBS, 0.05% Tween 20 using a Denley Well Wash 4 micro plate washer.

A BC-3 antibody solution was prepared by adding 4 μL of BC-3 antibody (0.405 mg/mL in PBS) to 2 mL of antibody dilution buffer (DB), which consisted of: 0.1 g BSA (Boehringer Mannheim Catalog 238–031), 10 mL 1×PBS, and 10 μL Tween 20. 100 μL of this solution was added to each well. The microplate strips were incubated for 1 hour at 25° C. The microplate wells were washed six times with 200 μL of 1×PBS, 0.05% Tween 20.

The secondary (detection) antibody solution was prepared by adding 4 μL of Goat anti-Mouse-HRP antibody conjugate (Pierce Cat#31430) (0.8 mg/mL in PBS) to 2 mL of antibody dilution buffer (DB). 100 μL of this solution was added to each well. The microplate strips were incubated for 1 hour at 25° C. The microplate wells were washed six times with 200 μL of 1×PBS, 0.05% Tween 20. TMB Substrate(100 μL per well, DAKO Cat S1600) was added and the microplate strips incubated at 25° C. for 15 minutes. The reaction was quenched with 100 μL of 1N HCl. The optical density was read at 450nm using a Molecular Devices Spectromax 250 microplate reader. By coating the jplate with the product peptide, one can create a standard curve which can be used to convert optical density values to units of activity.

ADMP activity can easily be followed by this method and inhibition of ADMP activity can be monitored. The $IC_{50}$ for the inhibition of ADMP by the hydroxamate inhibitor tested was 0.413 μM.

Example 2

HPLC Assay for Detection of ADMP Activity

The High Performance Liquid Chromatography (HPLC) instrument used for the assay was from Hewlett-Packard, model number HP1090, equipped with a HP ChemStation. A 250×4.6 mm Vydac $C_{18}$ column with 10 μ particle size was obtained from The Separations Group, Tesperia, Calif.; HEPES from Research Organics, Cleveland, Ohio; Brij-35 from Technicon Corp., Tarrington, N.Y.; Other chemicals from Sigma, St. Louis, Mo.; the lyophilized peptide substrate 41-PS, QTVTWPDMELPLRNITEGEARGS-VILTVKPIFEVSP SPL-(BIOTINYL)K (SEQ ID NO:4), which includes the ADMP E373-A374 cleavage site, was obtained from Quality Controlled Biochemicals, Inc. Hopkinton, Mass. A 21 amino acid product peptide (SEQ ID NO:5) with the sequence, ARGSVILTVKPIFEVSPSPL-(BIOTINYL)K, used as a standard for quantitation of product formation, was obtained from the same vendor.

The HPLC assay is performed in the following manner. The reaction buffer contains 50 mM HEPES, 10 mM $CaCl_2$, 100 mM NaCl and 0.05% Brij-35, pH 7.5. 30 μM 41-PS was incubated with 1 unit ADMP activity (1 unit=the amount of ADMP activity resulting in 1 pMole of 21-mer peptide product produced per hr at 37°) at 37° C. for 2.5 hours and then the reaction was quenched with 50 mM EDTA. A 10 μL portion of the reaction mixture was injected onto a reverse-phase HPLC $C_{18}$ column. The peptides were eluted with a mobile phase of 0.1% trifluoroacetic acid and a 25–45% acetonitrile gradient in 20 minutes. UV absorbance was measured at 220nm and peak integration was performed on a Hewlett-Packard HP ChemStation. The 21-mer product peptide was used as a standard for quantitation of product formation.The 41-PS and 21-mer product are well separated with retention times of 14.2 and 10.5 minutes, respectively.

Figure 1:
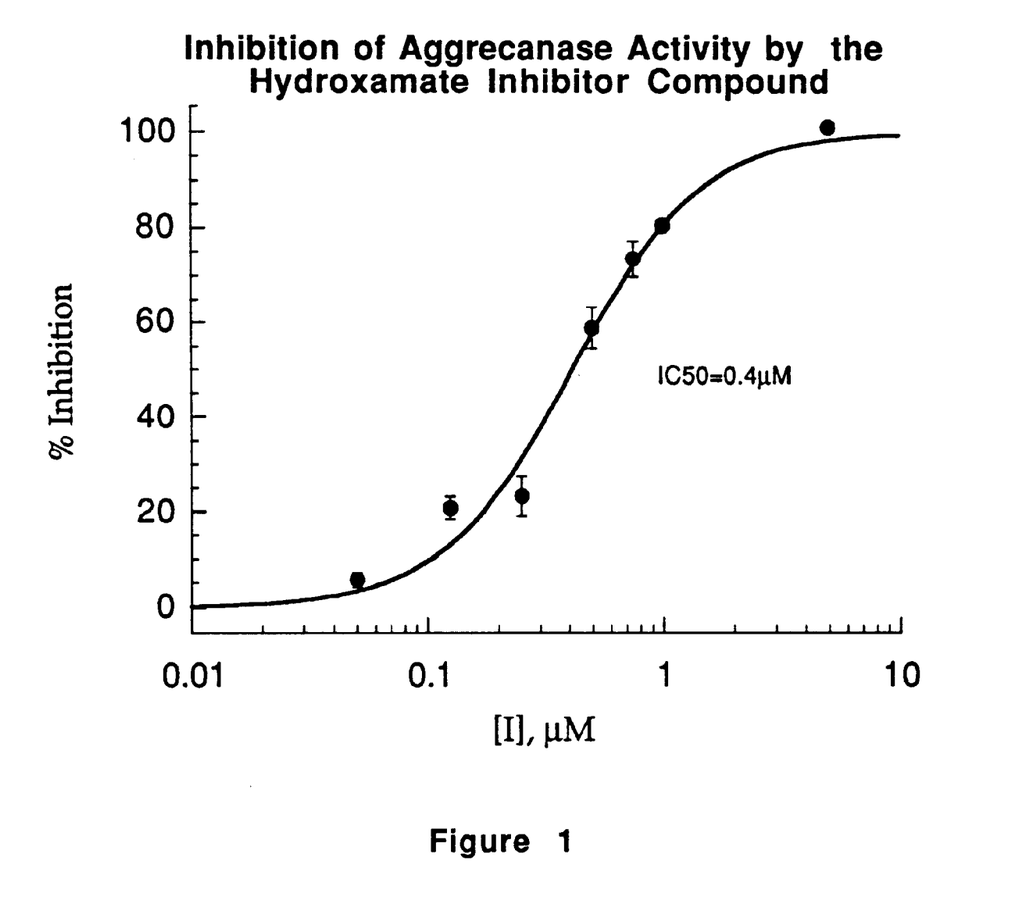
FIG. 1. Shows the activity of a biotinylated form of the 41-mer peptide substrate (41-PS) against ADMP enzymatic activity using the microplate assay format and the inhibition of that activity by a hydroxymate inhibitor compound.
Figure 2:
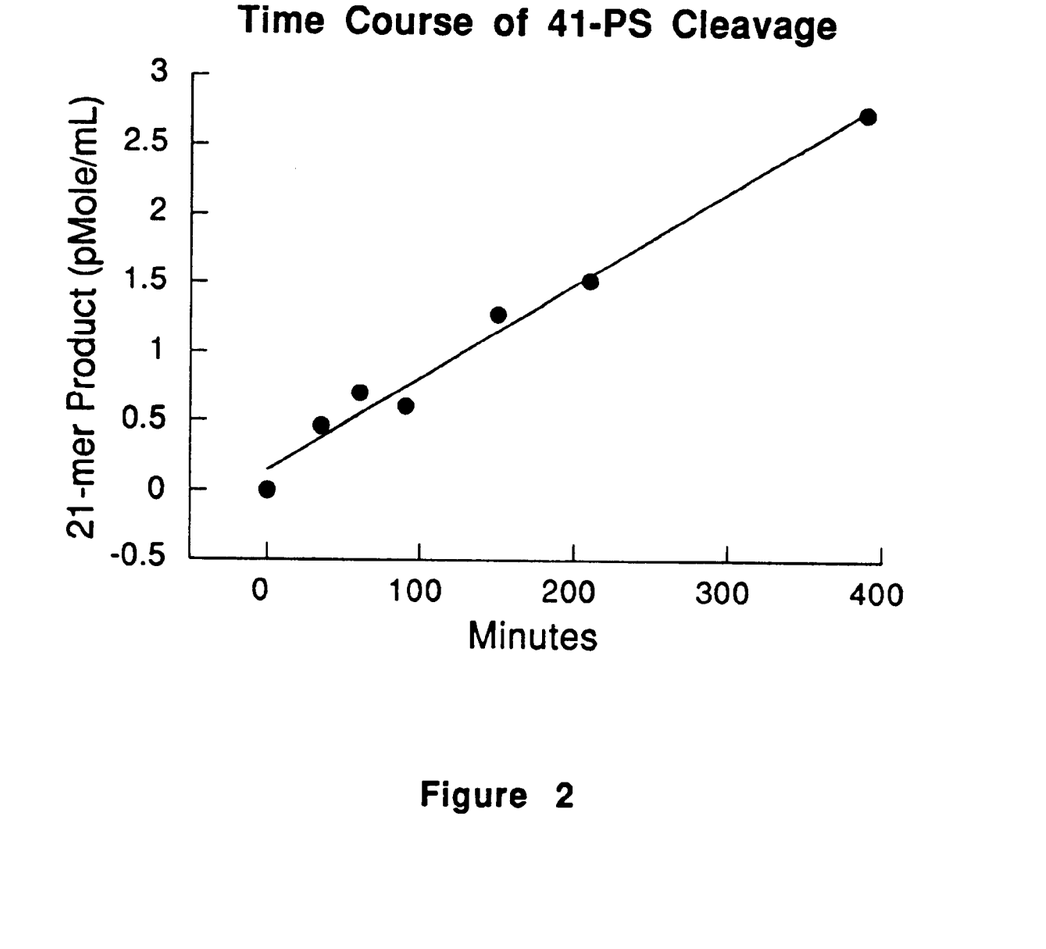
FIG. 2. Shows the activity of a biotinylated form of the 41-mer peptide substrate (41-PS) against ADMP enzymatic activity using the HPLC assay format.

A standard curve was prepared using the 21-mer peptide to allow quantitation of product formation. Effect of incubation time was evaluated and found to be linear over the time-course of the assay (FIG. 2).

Example 3

Inhibition of ADMP Activity by a Peptide Inhibitor

A peptide inhibitor was prepared based upon the sequence of the 40 amino acid peptide SEQ ID NO:1, but designed such that it contained a Glu to Gln substitution at the P1 of the Glu373-Ala374 bond. This peptide (30-IP) of the sequence:

QTVTWPDMELPLPRNITEGQARGSVILTVK-Biotin (SEQ ID NO:7) was prepared with the n-terminus acetylated and the c-terminal residue present as the amide (Quality Controlled Biochemicals, Inc., Hopkinton, Mass.). This peptide was employed in a microplate assay as described in Example 1 wherein the 30-IP inhibitor was substituted for the hydroxamate inhibitor used in that example. The 30-IP inhibitor was employed at final concentrations of 0.01, 0.1, 1.0, 3.0, 5.0, 10.0, 30.0 and 100.0 μM.

Figure 3:
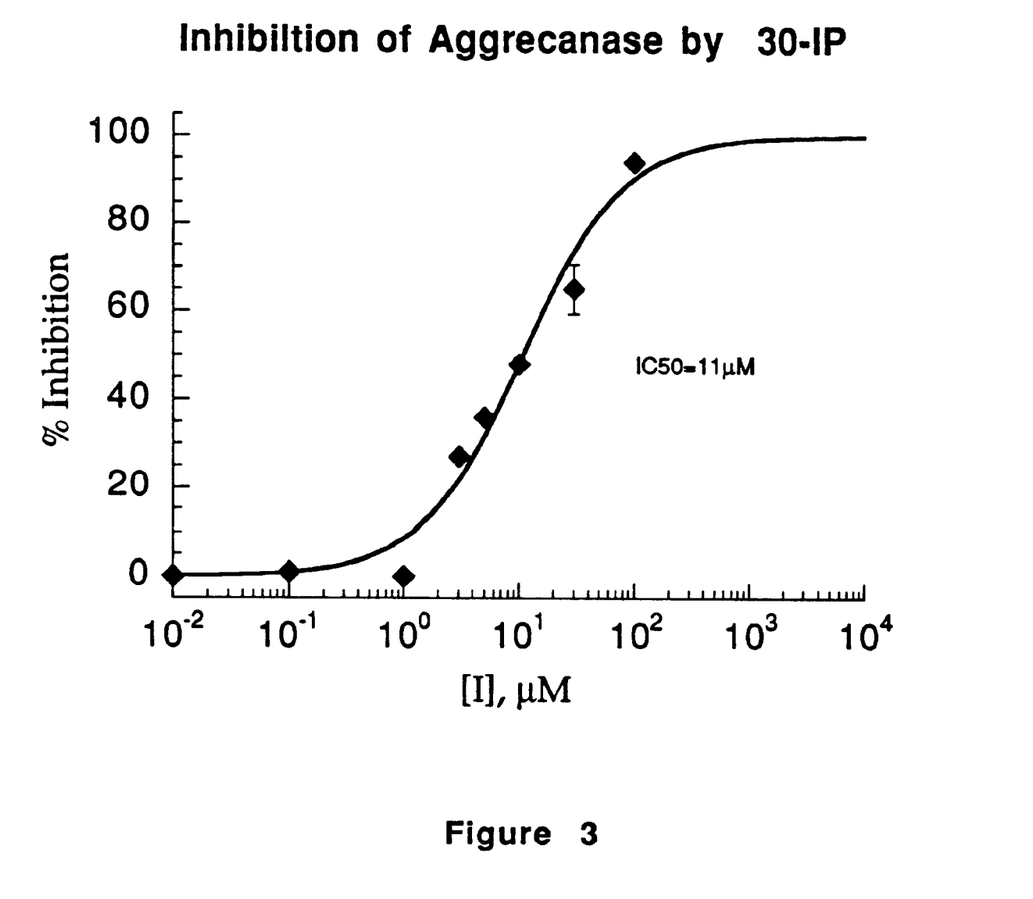
FIG. 3. Shows the activity of the biotinylated form of the 41-mer peptide substrate (41-PS) against ADMP enzymatic activity using the microplate assay format and the inhibition of that activity by the 30-mer inhibitor peptide (30-IP), QTVTWPDMELPLPRNITEGQARGSVILTVK-Biotin, the sequence of which is based upon the sequence of the 41-PS.

ADMP activity was inhibited as shown in FIG. 3. The $IC_{50}$ for the inhibition of ADMP activity by 30-IP was 11 μM.

Example 4

Problot Assay

This example describes a method for analyzing ADMP enzymatic activity and inhibitors of this activity by monitoring cleavage at the E373-A374 bond using the BC-3 antibody to detect fragments with the new N-terminus, ARGS. Samples containing ADMP activity (10 units/ml) were incubated with 500 nM bovine aggrecan monomer in a final volume of 200 μL in 0.05 M Tris, pH 7.6, containing 0.1 M NaCl and 10 mM $CaCl_2$. Reactions were incubated for 4 hr at 37° C., quenched with 20 mM EDTA, and analyzed for aggrecan fragments with the new N-terminus, ARGS, generated by specific ADMP-mediated cleavage using the Problot assay.

The Immobolin PVDF membrane plate (#MAIPN4550; Millipore Corp., Bedford, Mass.) was prewet with 50 μL per well 70% ethanol, incubated for 30 seconds at room temperature then flushed two times each with 200 μL of purified $H_2O$. The plate was then coated with aggrecan equivalent to 36 μg of glycosaminoglycan (GAG) as detected by the dimethyl methylene blue dye assay [Farndale R. W.,et al., (1982) Conn. Tiss. Res. 9, 247–248. ] in 150 μL of 50 mM carbonate-bicarbonate buffer, pH 9.6, overnight at 4° C. with gentle agitation. The coating solution was then filtered off of the plate using a vacuum manifold and membranes were washed once with 200 μL of Buffer A (Buffer A comprises 20 mM Tris, 500 mM NaCl, pH 7.5) allowing 20 seconds of contact with the membrane. Membranes were then blocked with 150 μL of 5% BSA/TBS solution for 1 hour at room temperature with gentle agitation. The blocking solution was filtered off of the plate and the membranes washed one time with 200 μL of 1×TBS buffer, allowing 20 seconds of contact with membrane per wash.

Removal of the glycosaminoglycan (GAG) side chains from aggrecan is necessary for the BC-3 antibody to recognize the epitope on the core protein. Therefore, to remove GAGs from the bound aggrecan, samples were treated with deglycosylation enzymes as follows: 0.01 units chondroitinase ABC (#EC4.2.2.4; Seikaguku Co., Kogyo, Japan) per 10 μg GAG in 150 μL of Buffer B (Buffer B comprises 50 mM sodium acetate, 100 mM NaCl, pH 6.5) was added to each well and incubated at 37° C. for 1 hour. Following incubation the enzyme solution was filtered out of the plate and 0.01 units chondroitinase ABC per 10 μg GAG, 0.01 units keratanase I (#EC3.2.1.103; Co., Kogyo, Japan) per 10 μg GAG, and 0.0005 units keratanase II (Seikaguku Co., Kogyo, Japan) per 10 μg GAG in 150 μL Buffer B were added and allowed to incubate an additional 2 hours at 37° C. Enzyme solution was filtered out and membranes rinsed one time with 200 μL of Buffer A.

150 μL of BC-3 antibody was added at a 1:500 dilution in 1% BSA in Buffer A and incubated for 1 hour at room temperature with gentle agitation. BC-3 antibody was removed and membranes washed three times each with 200 μL Buffer A allowing membrane contact for 20 seconds per wash. Next 150 μL of goat anti-mouse IgG AP conjugate (#S3721; Promega, Madison, WI) was added at a 1:2500 dilution in 1% BSA/TBS buffer and allowed to incubate for 1 hour at room temperature with gentle agitation. The secondary antibody was prefiltered prior to use, using 0.22 μM syringe filters to remove aggregates which cause high background. Following the incubation, secondary antibody was removed and wells were washed three times each with 200 μL Buffer A allowing contact for 20 seconds per wash. Then 100 μL of p-NPP AP substrate solution (# 50-80-00; Kirkegaard & Perry Lab., Gaithersburg, MD) was added to each well and incubated in the dark at room temperature for 30 minutes. The solution was then filtered into a corresponding ELISA plate. The filter plate was washed with 100 μL of 500 mM EDTA and the wash was combined with the corresponding samples in the ELISA plate. Absorbance of the samples was read at 405 nm (Thermomax plate reader).

By coating the plate with the target peptide, ARGS, linked to BSA representing the ADMP-generated product, one can create a standard curve which can be used to convert optical density values to units of activity. A unit of ADMP activity is defined as that resulting in product produced equivalent to 1 μg BSA peptide per hour at 37° C.

To evaluate inhibition of ADMP activity, compounds are prepared as 10 mM stocks in dimethyl sulfoxide (DMSO), water or other solvents and diluted to appropriate concentrations in water. Drug (50 μL) was added to 50 μL of 2 mg/mL aggrecan substrate and 50 μl of ADMP (40 units/ml) and brought to a final volume of 200 μL iby addition of 50 μl of 0.2 M Tris, pH 7.6, containing 0.4 M NaCl and 40 mM $CaCl_2$. The reaction mixture was incubated for 4 hr at 37° C., quenched with 20 mM EDTA and analyzed for ADMP-generated products. A sample containing enzyme and substrate without drug was included as a positive control and enzyme prequenched with EDTA served as a measure of background.

$IC_{50}$ values for inhibitors of ADMP enzymatic activity determined using the Problot assay with the BC-3 antibody for analysis of product generation by cleavage at the E373-A374 bond correlated ($r^2$=0.99) with those determined using a BC-3 Western blot analysis to detect product formation.

What is claimed is:

1. An assay for detecting the presence of aggrecan-degrading metalloproteinase activity in a sample comprising contacting the sample with an ADMP substrate peptide having an amino acid sequence selected from the group consisting of SEQ. ID. NO. 1, SEQ. ID. NO. 2 AND SEQ. ID. NO. 3, wherein cleavage of the peptide indicates the presence of said activity in the sample.

2. A method of assessing the activity of a compound for inhibiting the activity of an ADMP, said method comprising the steps of:

(a) measuring the activity of the ADMP in the absence of the compound according to the assay of claim 1; and, (b) measuring the activity of the ADMP in the presence of the compound according to the assay of claim 1, wherein the degree of difference between the ADMP activity measured in step (a) and the ADMP activity measured in step (b) indicates the ADMP inhibitory activity of the compound.

* * * * *

SEQUENCE LISTING

<160> NUMBER OF SEQ ID NOS: 7

<210> SEQ ID NO 1
<211> LENGTH: 40
<212> TYPE: PRT
<213> ORGANISM: Artificial Sequence
<220> FEATURE:
<221> NAME/KEY: PEPTIDE
<222> LOCATION: (1)..(40)
<223> OTHER INFORMATION: This 40 amino acid segment of the human
      aggrecan protein contains the ITEGE373-374ARGS cleavage site
      present in the natural protein substrate, aggrecan, and is capable
      of being cleaved at this specific recognition site by the ADMPs.

<400> SEQUENCE: 1

Gln Thr Val Thr Trp Pro Asp Met Glu Leu Pro Leu Pro Arg Asn Ile
 1               5                  10                  15

Thr Glu Gly Glu Ala Arg Gly Ser Val Ile Leu Thr Val Lys Pro Ile
                20                  25                  30

Phe Glu Val Ser Pro Ser Pro Leu
            35                  40

<210> SEQ ID NO 2
<211> LENGTH: 41
<212> TYPE: PRT
<213> ORGANISM: Artificial Sequence
<220> FEATURE:
<221> NAME/KEY: PEPTIDE
<222> LOCATION: (1)..(41)
<223> OTHER INFORMATION: This peptide substrate is based on a 41 amino
      acid segment of the bovine aggrecan protein and contains the
      E373-A374 cleavage site and is also capable of being cleaved at
      this specific recognition site by the ADMPs.

-continued

```
<400> SEQUENCE: 2

Gln Thr Val Thr Trp Pro Asp Val Glu Leu Pro Leu Pro Arg Asn Ile
1               5                   10                  15

Thr Glu Gly Glu Ala Arg Gly Ser Val Ile Leu Thr Ala Lys Pro Asp
            20                  25                  30

Phe Glu Val Ser Pro Thr Ala Pro Glu
        35                  40

<210> SEQ ID NO 3
<211> LENGTH: 40
<212> TYPE: PRT
<213> ORGANISM: Artificial Sequence
<220> FEATURE:
<221> NAME/KEY: PEPTIDE
<222> LOCATION: (1)..(40)
<223> OTHER INFORMATION: This 40 amino acid segment of the human
      aggrecan protein contains the KEEE1714-1715GLGS cleavage site
      present in the natural protein substrate, aggrecan, and is capable
      of being cleaved at this specific recognition site by the ADMPs.

<400> SEQUENCE: 3

Ile Thr Phe Val Asp Thr Ser Leu Val Glu Val Thr Pro Thr Thr Phe
1               5                   10                  15

Lys Glu Glu Glu Gly Leu Gly Ser Val Glu Leu Ser Gly Leu Pro Ser
            20                  25                  30

Gly Glu Leu Gly Val Ser Gly Thr
        35                  40

<210> SEQ ID NO 4
<211> LENGTH: 41
<212> TYPE: PRT
<213> ORGANISM: Artificial Sequence
<220> FEATURE:
<221> NAME/KEY: PEPTIDE
<222> LOCATION: (1)..(41)
<223> OTHER INFORMATION: This sequence was prepared as a biotin
      conjugate by adding a Lys residue at the carboxy terminus of the
      peptide SEQ ID NO:1. Biotin was then covalently attached through
      the lysine amino side chain, i.e., there is a biotinylated lysine
      residue at position 41.

<400> SEQUENCE: 4

Gln Thr Val Thr Trp Pro Asp Met Glu Leu Pro Leu Pro Arg Asn Ile
1               5                   10                  15

Thr Glu Gly Glu Ala Arg Gly Ser Val Ile Leu Thr Val Lys Pro Ile
            20                  25                  30

Phe Glu Val Ser Pro Ser Pro Leu Xaa
        35                  40

<210> SEQ ID NO 5
<211> LENGTH: 21
<212> TYPE: PRT
<213> ORGANISM: Artificial Sequence
<220> FEATURE:
<221> NAME/KEY: PEPTIDE
<222> LOCATION: (1)..(21)
<223> OTHER INFORMATION: This 21 amino acid peptide representing the
      product of ADMP mediated cleavage of SEQ ID NO:4 containing the
      ARGS N-terminus was prepared in a similar manner to SEQ ID NO:4
      and has a biotinylated lysine residue at position 21.

<400> SEQUENCE: 5

Ala Arg Gly Ser Val Ile Leu Thr Val Lys Pro Ile Phe Glu Val Ser
1               5                   10                  15

Pro Ser Pro Leu Xaa
```

```
<210> SEQ ID NO 6
<211> LENGTH: 21
<212> TYPE: PRT
<213> ORGANISM: Artificial Sequence
<220> FEATURE:
<221> NAME/KEY: PEPTIDE
<222> LOCATION: (1)..(21)
<223> OTHER INFORMATION: This 21 amino acid peptide representing the
      product of ADMP mediated cleavage of SEQ ID NO:4 was prepared in a
      similar manner to SEQ ID NO:4 and has a biotinylated lysine
      residue at position 1.

<400> SEQUENCE: 6

Xaa Gln Thr Val Thr Trp Pro Asp Met Glu Leu Pro Leu Pro Arg Asn
1               5                   10                  15

Ile Thr Glu Gly Glu
            20

<210> SEQ ID NO 7
<211> LENGTH: 30
<212> TYPE: PRT
<213> ORGANISM: Artificial Sequence
<220> FEATURE:
<221> NAME/KEY: PEPTIDE
<222> LOCATION: (1)..(30)
<223> OTHER INFORMATION: This peptide inhibitor was prepared based upon
      the sequence of the 40 amino acid peptide SEQ ID NO:1, but
      designed such that it contained a Glu to Gln substitution at the
      P1 of the Glu373-Ala374 bond, and has a biotinylated lysine
      residue at position 30.

<400> SEQUENCE: 7

Gln Thr Val Thr Trp Pro Asp Met Glu Leu Pro Leu Pro Arg Asn Ile
1               5                   10                  15

Thr Glu Gly Gln Ala Arg Gly Ser Val Ile Leu Thr Val Xaa
            20                  25                  30
```